United States Patent [19]

Serrao

[11] Patent Number: 4,524,768
[45] Date of Patent: Jun. 25, 1985

[54] RESTRAINT GARMENT

[75] Inventor: Charles A. Serrao, Montreal, Canada

[73] Assignee: Giovanni Argentino, Verdun, Canada

[21] Appl. No.: 534,294

[22] Filed: Sep. 21, 1983

[51] Int. Cl.³ ............................................. A61F 13/00
[52] U.S. Cl. ...................................................... 128/134
[58] Field of Search ................................. 128/134, 133

[56] References Cited

U.S. PATENT DOCUMENTS

| 1,944,451 | 1/1934 | Newman | 128/133 |
| 2,439,658 | 4/1948 | Holloway | 128/134 |
| 2,465,622 | 3/1949 | Widetsky | 128/134 |
| 2,481,741 | 9/1949 | Graves | 128/134 |
| 2,940,443 | 6/1960 | Baker | 128/134 |
| 3,502,073 | 3/1970 | Stanley | 128/134 |

Primary Examiner—John D. Yasko
Assistant Examiner—Christa K. Scott
Attorney, Agent, or Firm—Robic, Robic & Associates

[57] ABSTRACT

An improved restraint garment made from mesh material and having a torso enclosing portion with a top edge defining a neck opening. Arm and leg enclosing portions are integral with the torso enclosing portion and project therefrom. Closures extend from the end of each arm and leg enclosing portion through the torso enclosing portion to its top edge. Restraint members are provided at the shoulder areas of the garment, and at the ends of the arm and leg enclosing portions, for use in substantially immobilizing the garment on a bed.

7 Claims, 6 Drawing Figures

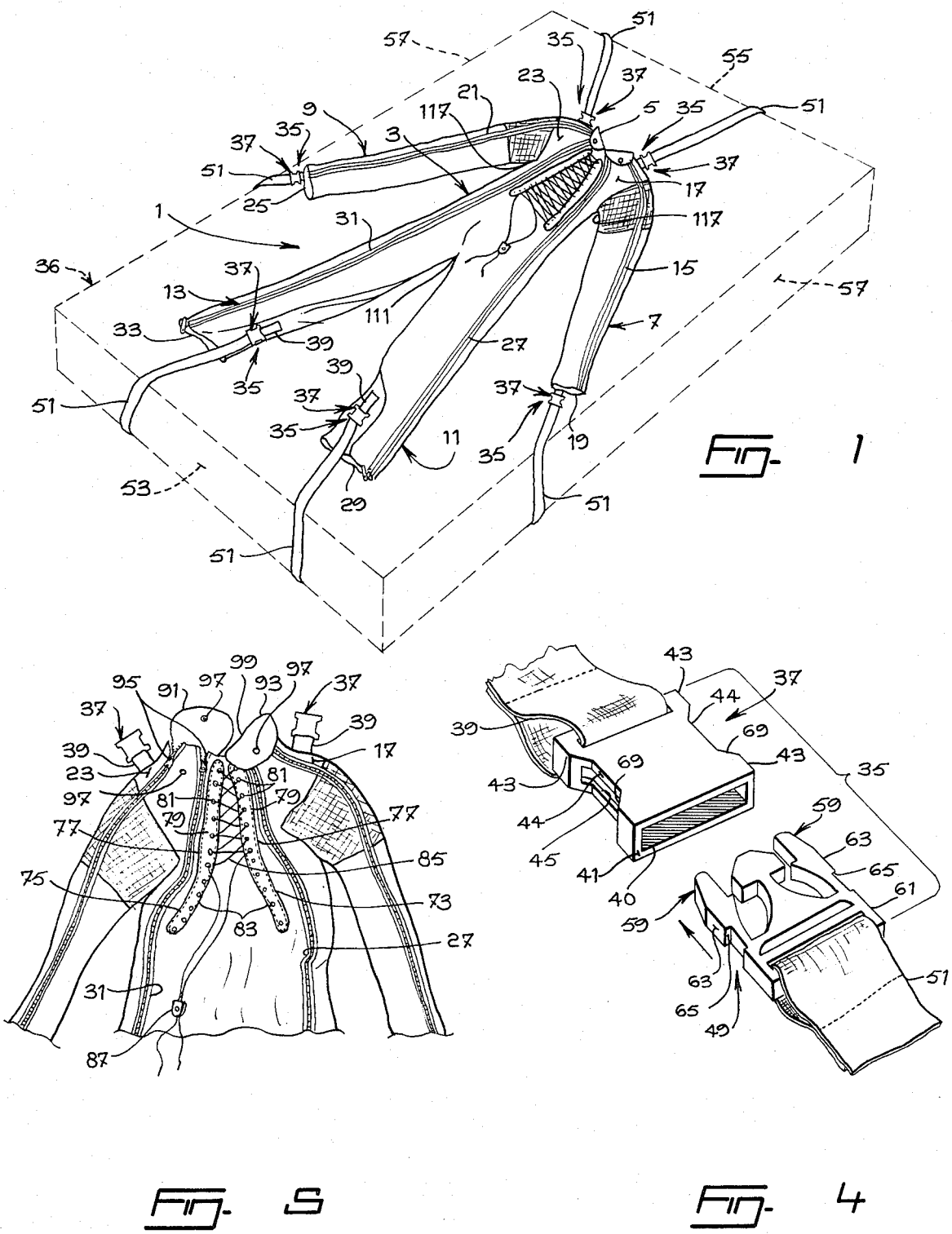

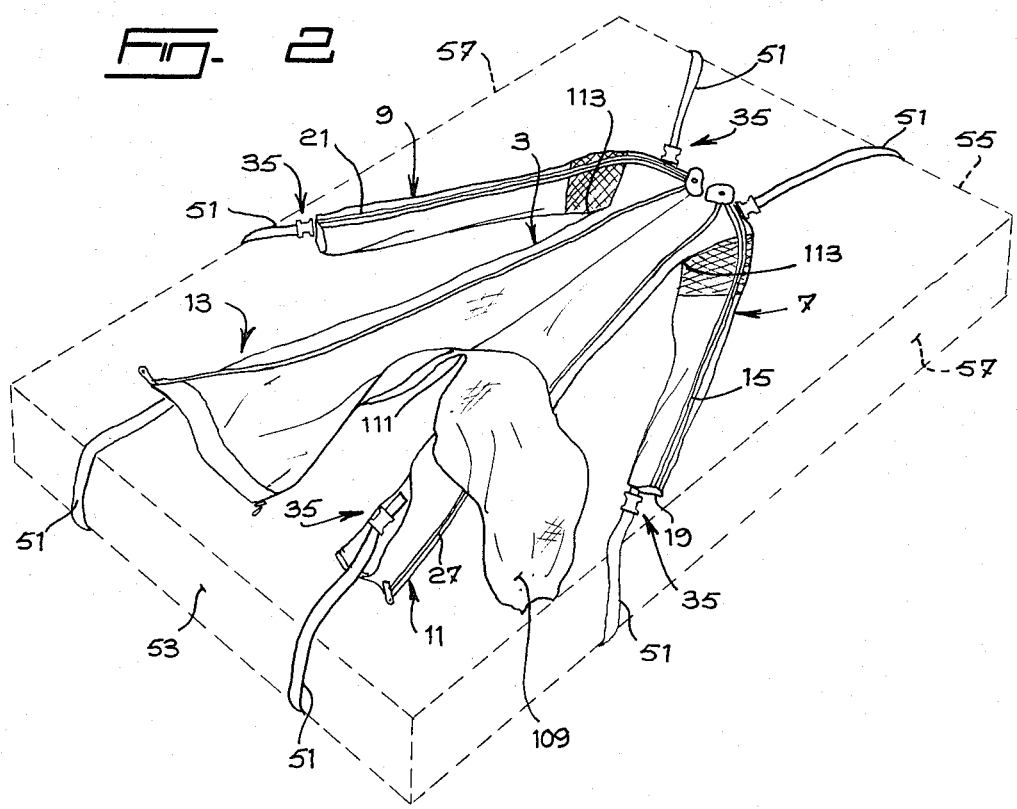
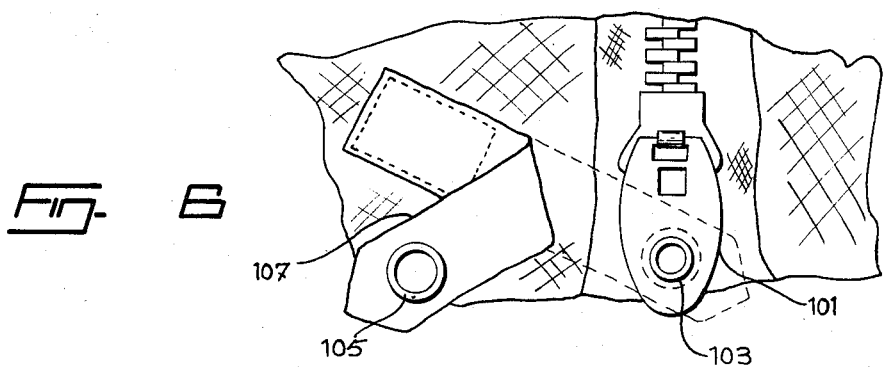
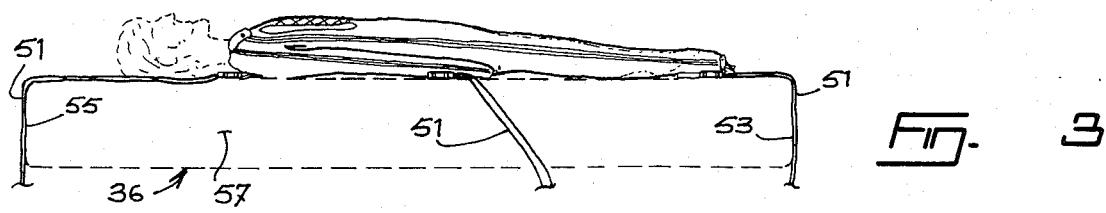

RESTRAINT GARMENT

The present invention relates to an improved restraint garment.

Restraint garments are used to substantially immobilize patients on a bed. Such patients might, for example, be people suffering from such diseases that they are liable to injure themselves if not restrained.

Different kinds of restraint means are already known, which all have some disadvantages. One of these known restraint means consists of cuff members on the ankles and wrists to immobilize the limbs of a patient. In use, the cuff members are tightly tied and can injure the limbs when the patient involuntarily fights against his restraints. Straps are also commonly employed as restraint means. In use, the straps are extended across the torso to restrain a patient and often make it difficult for the patient to breathe. Restraint garments are also known. Such garments are difficult to place on a person, and make access to any one part of the patient's body, to treat that part, difficult. Many garments also can only be used in a face-up position. In a more general manner, almost all the known restraint means, including garments, are difficult to undo if an emergency should arise and the patient has to be quickly moved.

A first object of the present invention is to provide an improved restraint garment which securely, yet comfortably, restrains a patient.

Another object of the present invention is to provide an improved restraint garment which, while still securely restraining a patient, provides easy access to different parts of the patient's body.

A further object of the present invention is to provide a restraint garment which minimizes the risk of a restrained patient injuring himself.

A further object of the present invention is to provide a restraint garment which can be easily released in an emergency.

Yet another object of the present invention is to provide a restraint garment which can be easily cleaned.

The restraint garment of the present invention comprises a torso enclosing portion with a neck opening, and integral arm and leg enclosing portions extending from the torso portion. Closure means extend from the free end of each arm and leg portion to the neck opening through the torso portion. Each closure means preferably comprises a zipper having a slider at each end of the zipper. The arrangement of the closure means allows the garment to be easily put on, or taken off a person. The closure means on the arm and leg enclosing portions also allows these portions to be opened independently of the rest of the garment providing ready access to any part of the person's limbs.

The restraint garment is provided with a first restraint member on each side of the neck opening and a first restraint member at the free end of each arm and leg portion. The first restraint members are adapted to cooperate with second restraint members on the end of strap members mounted on a bed in a manner to substantially immobilize the garment on the bed. The first and second restraint members are constructed to be quickly and easily connected and disconnected together. This permits a restrained patient to be quickly released in any emergency. The garment is restrained in a manner so that its armpit and crotch areas prevents a person within the garment from sliding down in the garment, and so that its shoulder areas adjacent the neck opening prevent a person from sliding up in the garment.

The arm portions are preferably made longer than the length of a person's arm so that the restrained person cannot reach the slider of the closure means, or the restraint member, at the free end of the arm portion.

The garment can be made from a soft, light, yet strong, mesh material which can be easily cleaned. The mesh material also allows air to circulate through the garment. The mesh material provides more uniform pressure over the entire body of a patient while restraining him when compared to the pressure applied by cuffs and straps, and thus is more comfortable and less likely to injure the restrained patient.

The invention is particularly directed toward a restraint garment having a torso enclosing portion with a top edge defining a neck opening. Two arm enclosing portions and two leg enclosing portions are integral with the torso enclosing portion, and each extends therefrom to terminate in a free end. Closure means are provided in the garment to access into it. Restraint means are also provided on the garment for attaching it onto a bed in view of substantially immobilizing a patient on this bed.

The invention will be better understood upon reading of the following non-restrictive description of a preferred embodiment there of, made with reference to the accompanying drawings in which:

FIG. 1 is a perspective view of a restraint garment according to the invention in a restrained position;

FIG. 2 is a view similar to FIG. 1 but with a portion of the garment undone;

FIG. 3 is a side elevation view of the garment in use;

FIG. 4, appearing on the same sheet as FIG. 1, is a detail view of the restraint means;

FIG. 5, appearing on the same sheet as FIG. 1, is a detail view of the front upper portion of the garment; and FIG. 6 is a detail view of a closure retainer.

The restraint garment 1, as shown in FIGS. 1 to 3 comprises a torso enclosing portion 3 with a top edge 5 defining a neck opening. It also comprises a pair of arm enclosing portions 7 and 9 integral with the torso enclosing portion 3 and extending therefrom, and a pair of leg enclosing portions 11 and 13 integral with the torso enclosing portion 3 and extending therefrom.

To provide access to the garment 1, a number of closures are provided, which allow the garment to be opened up. First closure means 15 extend from one side of the top edge 5 defining the neck opening, through one shoulder area 17 of the torso portion 3 and along the outside of one arm portion 7 to its free end 19. A second closure means 21 extends from the other side of the top edge 5 defining the neck opening, through the other shoulder area 23 of the torso portion 3, and along the outside of the other arm portion 9 to its outer end 25. A third closure means 27 extends down from the top edge 5 along one side of the front of the torso portion 3, and continues down the outside of one leg portion 11 to its outer end 29. A fourth closure means 31 extends down from the top edge 5 along the other side of the front of the torso portion 3, and continues down the outside of the other leg portion 13 to its outer end 33. Each of the four closure means 15, 21, 27 and 31 preferably comprises a zipper having top and bottom slides as will be described.

Restraint means 35 are provided for use in holding the garment substantially immobile on a bed 36, as shown in FIG. 1, and thus holding a person in the garment substantially immobile. The restraint means 35 include first restraint members 37 fixed to the garment 1 at certain locations with a short strap 39. In more detail, a pair of first restraint members 37 are fixed to the torso portion 3, one at the top of each shoulder area 17, 23 on each side of the neck opening. A first restraint member 37 is also fixed to each arm portion 7, 9 adjacent its free end 19, 25 respectively. A first restraint member 37 is further fixed to each leg portion 11, 13 adjacent its free end 29, 33 respectively. The first restraint member 37, as shown in FIG. 4, has a socket 40 extending inwardly from its outer end 41. The sides 43 of the restraint member are notched, as shown at 44, to provide side openings 45 to the socket 40.

The restraint means 35 includes a second restraint member 49 in the form of a latch cooperating with the first restraint member 37. The second restraint member 49 is attached at one end to the end of a strap 51 fastened to the bed 36 on which a person is to be restrained. As shown in FIGS. 1 to 3, a first pair of straps 51 extend up from the bottom end 53 of the bed; a second pair of straps 51 extend up from the top end 55 of the bed, and a single strap 51 extends up from each side 57 of the bed, near its bottom end 53 and angled toward the top end 55 of the bed. Each second restraint member 49, as shown in FIG. 4, has a pair of resilient fingers 59 extending forwardly from its main body 61. Each finger 59 is notched on its outer side 63 to provide a stop shoulder 65. When the second restraint member 49 is inserted into the socket 40 on a cooperating first restraint member 37, the resilient fingers 59 are initially bowed toward each other. Once the fingers 59 reach the side openings 45 in the first restraint member 3; they move outwardly to their normal position and the top shoulders 65 cooperate with the forward edges 69 of the notches 44 to lock the second restraint member 49 in the first restraint member 37.

The second restraint member 49 is easily removed from the first restraint member 37 by squeezing the resilient fingers 59 toward each other, where they project in the notches 44, to move the stop shoulders 65 off edges 69; and simultaneously sliding the second restraint member 49 outwardly. It will be seen that the restraint means 35 allow the garment 1 to be easily attached to, or detached from, the bed 36. In addition, a single arm or leg portion of the garment 1 can be attached to, or detached from, the bed 36 independently of the other portions of the garment 1.

Means are provided on the garment 1 for adjusting the size of the upper part of the torso enclosing portion 3. The size adjusting means include a pair of flexible strips 73 and 75 attached to the front of the garment as shown in FIG. 5. One strip 73 extends down from the top edge 5 defining the neck opening, adjacent closure means 27, and the other strip 75 extends down from the top edge 5 adjacent closure means 31. Each strip 73, 75 is fastened to the garment along its outer side 77 by one or more lines 79 of stitching. A row of eyelets 81 is provided in each strip 73, 75 along its length between its inner side 83 and the line 79 of stitching. A lace 85 is threaded alternatively through the eyelets 81 in both strips 73, 75, as shown in FIG. 5. The ends of the lace 85 are joined by a quick release fastener device 87. Normally the lace 85 is loosely threaded through the eyelets 81. However the lace 85 can be tightened drawing the strips 73, 75 toward each other and thus making the upper section of the torso enclosing portion 3 smaller. In this manner, the torso enclosing portion can be adjusted to tightly fit a person to be restrained.

Cushion pads 91 and 93 are provided on the garment 1 at its top edge 5. One pad 91, as shown in FIG. 5, is fastened to the inside of the garment 1 on one front side of the top edge 5, and a second pad 93 is fastened to the inside of the garment 1 on the other front side of the top edge 5, adjacent the first pad 91. The pads 91, 93 fold over the top edge 5 defining the neck opening to cover the top sliders 95 on the zipper closure means 15, 21, 27, 31 and fasten to the front of the garment via snap fasteners 97. The folded edge 99 of each pad 91, 93 is soft and protects the neck and throat of a restrained person.

Each zipper closure means 15, 21, 27 and 31 also has a bottom slider 101 as shown in FIG. 6. Each bottom slider 101 has a snap fastener element 103 thereon which cooperates with a snap fastener element 105 on a short strap 107 fastened to the end of each arm and leg enclosing portion adjacent its respective closure means. When the strap 107 is fastened to the slider 101 via fastener elements 103, 105, the slider 101 is held in place and prevented from inadvertently moving up the leg or arm enclosing portions to open them.

The top and bottom sliders 95, 101 on the zipper closure means allow the garment 1 to be easily opened for entry or exit therefrom. As shown in FIG. 2, the front portion 109 of the torso enclosing portion 3 can be opened down to the crotch portion 111 by sliding the top sliders 95 on zipper closures 27, 31 down to the bottom of the leg enclosing portions 11, 13. The shoulder portions 17, 23 can also be opened by sliding down the top sliders 95 on zipper closures 15, 27 and 31 respectively. The bottom sliders 101 on closures 15, 21 and 27, 31 also allow a single limb to be treated without having to remove all restraints. Thus if an injured wirst needs treatment, the zipper closure on the arm enclosing portion of the garment restraining that arm can be opened up from its outer free end by moving its bottom slider 101 up slightly thus opening up the bottom part of the arm enclosing portion to provide access to the wrist.

The garment 1 can be made from a soft, yet strong, mesh material. The mesh material preferably is nylon, and keeps the restrained person cool, yet is lightweight and can be easily and quickly washed and dried. The arm enclosing portions 7 and 9 of the garment are made extra long. They can, for example, be forty inches long. This prevents the restrained person's hand from reaching out of the arm enclosing portions to release the restraint means, or the bottom zipper slide, or to grab at objects or persons.

The straps 39 and 51 can be made of an semi-rigid elastic material to permit some movement of the patient's body.

When the restraint garment is laid out as shown in FIG. 1, a person within the garment cannot slide the garment down, because of the top restraint means 35 on the soulder portions 17 and 23 of the garment, and cannot slide the garment up because of bottom restraint means 35 on the free ends of the leg enclosing portions 11, 13. The straps 51 on these restraint means are angled toward the corners of the bed and thus also hold the person from moving the either side. The crotch 111 of the garment, and the armpits 113, prevent the person from sliding down within the garment. The shoulder portions 17 and 23 adjacent the neck opening, prevent the person from sliding up out of the garment. If necessary, the crotch 111, the armpits 113, and the shoulder areas 17, 23 of the garment can be reinforced with patches fixed to the garment.

If desired, both arms and legs enclosures can be made larger than the arms and legs of the patient.

The embodiments of the invention in which an exclusive property or privilege is claimed are defined as follows:

1. A restraint garment for securely, yet confortably, immobilize a patient in laid down position on a bed, said garment comprising:
   a torso enclosing portion with a top edge defining a neck opening;
   two arm enclosing portions and two leg enclosing portions integral with the torso enclosing portion and extending therefrom to terminate in free ends, said arm enclosing portions being made longer than the normal length of an arm;
   closure means in the garment for providing access into it; and
   restraint means on the garment for attaching it into the a bed in view of substantially immobilizing a patient within the garment on said bed, said restraint means comprising a plurality of first restraint members respectively fixed to the garment on each side of the neck opening and at the free end of each arm and leg enclosing portion, said first restraint members being detachably connectable to a similar number of second restraint members mounted at the end of straps fixed to the bed in such a manner as to substantially immobilize said garment and the patient therein in laid down position on said bed.

2. A restraint garment as claimed in claim 1, wherein said closure means comprises a closure extending from the free end of each arm and leg enclosing portion, through the torso enclosing portion to the top edge defining the neck opening.

3. A restraint garment as claimed in claim 2, wherein each closure extends along the outside of the arm and leg enclosing portions.

4. A restraint garment as claimed in claim 3, wherein each closure comprises a zipper having a slider at each end.

5. A restraint garment as claimed in claim 2, including means on the front of the torso portion of the garment for use in adjusting its size.

6. A restraint garment as claimed in claim 1, wherein the size adjusting means comprises: two flexible strips of material fastened one on each side of the front of the torso enclosing portion, each strip extending down from the neck opening and fastened along its outer side to the garment, and a row of eyelets in each strip; and a lace threaded alternatively through the eyelets on both strips.

7. A restraint garment as claimed in claim 2, made from a mesh material.

* * * * *